US006329430B1

(12) United States Patent
Regan (10) Patent No.: US 6,329,430 B1
(45) Date of Patent: *Dec. 11, 2001

(54) MODULATION OF N-METHYL-D-ASPARTATE RECEPTOR RESPONSES WITH S-SUBSTITUTED DERIVATIVES OF GLUTATHIONE

(75) Inventor: Raymond F. Regan, Wayne, PA (US)

(73) Assignee: Thomas Jefferson University, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/376,530

(22) Filed: Aug. 18, 1999

(51) Int. Cl.$^7$ ................................................. A61K 31/195

(52) U.S. Cl. ............................................................ 514/562

(58) Field of Search ............................................. 514/562

(56) References Cited

PUBLICATIONS

Bains et al, Embase Abstracts Online, No. 1998049879, 1997.*
Aizenman E., et al., "Selective Modulation Of NMDA By Reduction And Oxidation".*Neuron*, vol. 2, pp. 1257–1263, (1989).
Gilbert K.R., et al., "Oxidized Glutathione Modulates N–Methyl–D–Aspartate–And Depolarization–Induced Increases In Intracellular $Ca^{2+}$ In Cultured Rat Forebrain Neurons", *Neurosci. Lett*, vol. 133, pp. 11–14, (1991).
Guo N. and Shaw C., "Characterization And Localization of Gluthathione Binding Sites On Cultured Astrocytes", *Mol. Brain Res.*, vol. 15, pp. 207–215, (1992).
Janáky R., et al., "Glutathione Modulates The N–Methyl–D–Aspartate Receptor–Activated Calcium Influx Into Cultured Rat Cerebellar Granule Cells", *Neurosci. Lett.*, vol. 156, pp. 153–157, (1993).
Lanius R.A., et al., "Characterization, Distribution, And Protein Kinase C–Mediated Regulation of [$^{35}$S]Glutathione Binding Sites In Mouse And Human Spinal Cord", *J. Neurochem.*, vol. 63, pp. 155–160, (1994).
Ogita K. and Yoneda Y., "Temperature–Dependent And — Independent Apparent Binding Activities Of [$^3$H]Glutathione In Brain Synaptic Membranes", *Brain Res.*, vol. 463, pp. 37–46. (1988).
Shaw C.A., et al., "Glutathione–Induced Sodium Currents In Neocortex", *Neuroreport*, vol. 7, pp. 1149–1152, (1996).
Sucher N.J. and Lipton S.A., "Redox Modulatory Site Of The NMDA Receptor–Channel Complex: Regulation By Oxidized Glutathione", *J. Neurosci. Res.*, vol. 30, pp. 582–591. (1991).
Varga V., et al., "Glutathione Is An Endogenous Ligand Of Rat Brain N–Methyl–D–Aspartate (NMDA) And 2–Amino–3–Hydroxy–5–Methyl–4–Isoxazolepropionate (AMPA) Receptors", *Neurochem. Res.*, vol. 22, pp. 1165–1171, (1997).
Zängerle L., et al. "Screening Of Thiol Compounds: Depolarization–Induced Release Of Glutathione And Cysteine From Rat Brain Slices", *J. Neurochem.*, vol. 59, pp. 181–189, (1992).

* cited by examiner

*Primary Examiner*—William R. A. Jarvis
(74) *Attorney, Agent, or Firm*—Janet B. Smith (57) ABSTRACT

The present invention involves a method of treating pain, neurological diseases and neuronal injury in a mammal by utilizing compounds that interact with and modify one of the redox sites of the N-methyl-D-aspartate (NMDA) receptor in said mammal. These compounds include S-substituted derivatives of glutathione which modulate or regulate the NMDA glutamate receptor.

1 Claim, 10 Drawing Sheets

MODULATION OF N-METHYL-D-ASPARTATE RECEPTOR RESPONSES WITH S-SUBSTITUTED DERIVATIVES OF GLUTATHIONE

FIELD OF INVENTION

The present invention relates generally to the field of neurology and to a method of treating pain, neurological diseases and neuronal injury and, more particularly, to the use of S-substituted derivatives of glutathione to modulate or regulate the N-methyl-D-aspartate (NMDA) glutamate receptor.

BACKGROUND OF THE INVENTION

Glutathione is a predominant intracellular antioxidant, and is present in CNS cells in millimolar concentrations. (Orlowski M. and Karkowski A., Glutathione metabolism and some possible functions of glutathione in the nervous system. *Int Rev Neurobiol* 19: 75–121, 1976). Cell turnover of this tripeptide is surprisingly rapid, due at least in part to release of its reduced form (GSH) into the extracellular space. (Yudkoff M., Pleasure D., Cregar L., Lin Z. P., Nissim I., Stem J. and Nissim I., Glutathione turnover in cultured astrocytes: studies with [$^{15}$N]glutamate. *J Neurochem* 55: 137–145, 1990). GSH release under resting conditions is quantitatively comparable to that of the excitatory neurotransmitters glutamate and aspartate, and is increased by neuronal depolarization via a calcium-dependent process. (Zangerle L., Cuenod M., Winterhalter K. H. and Do K. Q., Screening of thiol compounds: depolarization-induced release of glutathione and cysteine from rat brain slices. *J Neurochem* 59: 181–189, 1992). The role of extracellular glutathione has not been defined, and has been the subject of considerable conjecture. Until recently, it was presumed to function as an antioxidant and/or an amino acid transporter. GSH alone, without glutathione peroxidase, directly reacts with both the hydroxyl radical and aldehyde products of lipid peroxidation, and may therefore protect cell membranes and associated protein sulfhydryl groups from free radical attack. (Halliwell B. and Gutteridge J. M. C., *Free Radicals in Biology and Medicine* 2nd ed., pp. 30, 80, 210, Oxford University Press, 1989). γ-glutamyl transpeptidase is primarily located on the outer cell membrane and converts glutathione into gamma-glutamyl amino acids and cysteinylglycine, which are then rapidly transported into cells. (Dringen R., Kranich O., Loschman P. A. and Hamprecht B., Use of dipeptides for the synthesis of glutathione by astroglia-rich primary cultures. *J Neurochem* 69: 868–74, 1997; Meister A. and Anderson M. E., Glutathione. *Annu Rev Biochem* 52: 711–760, 1983). Extracellular GSH may therefore serve as a safe carrier molecule for its constituent amino acids (glutamate, cysteine, and glycine), all of which are synaptically active.

A growing body of experimental evidence suggests that extracellular GSH may also specifically interact with membrane receptors on neurons and glia. High affinity, saturable GSH binding sites have been demonstrated in both the rodent and human CNS. (Lanius R. A., Shaw C. A., Wagey R. and Krieger C., Characterization, distribution, and protein kinase C-mediated regulation of [$^{35}$S]glutathione binding sites in mouse and human spinal cord. *J Neurochem* 63: 155–160, 1994; Ogita K. and Yoneda Y., Temperature-dependent and -independent apparent binding activities of [$^3$H]glutathione in brain synaptic membranes. *Brain Res* 463: 37–46, 1988). Binding is enhanced by protein kinase C activation and is selectively inhibited by cysteine and S-hexylglutathione but not by glutamate. The similar distribution of GSH and glutamate binding sites (Ogita K. and Yoneda Y., Temperature-dependent and -independent apparent binding activities of [$^3$H]glutathione in brain synaptic membranes. *Brain Res* 463: 37–46, 1988) suggests that GSH may act as a neuropeptide at the redox site of the NMDA receptor. GSH potentiated responses to glutamate in cells expressing recombinant NR1-NR2A receptors (Kohr G., Eckardt S., Luddens H., Monyer H. and Seeburg P. H., NMDA receptor channels: subunit-specific potentiation by reducing agents. *Neuron* 12: 1031–1040, 1994), and increased glutamate and NMDA-induced calcium influx in cultured cerebellar granule cells. (Janaky R., Varga V., Saransaari P. and Oja S. S., Glutathione modulates the N-methyl-D-aspartate (NMDA) receptor-activated calcium influx into cultured rat cerebellar granule cells. *Neurosci Lett* 156: 153–157, 1993).

Excessive activation of glutamate receptors increases neuronal oxidative stress (Monyer H., Hartley D. M. and Choi D. W., 21-aminosteroids attenuate excitotoxic neuronal injury in cortical cell cultures. *Neuron* 5: 121–126, 1990; Puttfarcken P. S., Getz R. L. and Coyle J. T., Kainic acid-induced lipid peroxidation: protection with butylated hydroxytoluene and U78517F in primary cultures of cerebellar granule cells. *Brain Res* 624: 223–232, 1993; Reynolds I. J. and Hastings T., Glutamate induces the production of reactive oxygen species in cultured forebrain neurons following NMDA receptor activation. *J Neurosci* 15: 3318–3327, 1995) and has been implicated in the pathogenesis of both acute CNS insults and neurodegenerative diseases (Lipton S. A. and Rosenberg P. A., Excitatory amino acids as a final common pathway for neurologic disorders. *N Engl J Med* 330: 613–622, 1994). While screening antioxidant compounds in a cell culture model of mild excitotoxic injury, marked potentiation of NMDA neurotoxicity by glutathione was unexpectedly observed, consistent with it being a ligand at the NMDA receptor redox site.

The NMDA glutamate receptor may predominate in many disease processes because of the high calcium permeability of its cation channel. One promising method of preventing NMDA receptor overactivation is the pharmacologic modulation of its redox sites. However, since the endogenous ligands at these sites had been unknown, little progress had been reported. Recent results identify glutathione and L-cysteine as endogenous ligands at the redox sites of the NMDA receptor.

The present invention is a method of treating central nervous system diseases and conditions in a mammal, comprising administering a compound that interacts with and modifies one of the redox sites of the NMDA receptor in said mammal. In the present invention, two S-substituted glutathione derivatives S-hexylglutathione and S-methylglutathione, blocked the potentiation of NMDA receptor neurotoxicity produced by reducing agents. Thus, glutathione derivatives provide a novel pharmacologic approach to modulation of NMDA receptor responses.

Present pharmacologic approaches to the NMDA receptor include: 1) competitive antagonists, which are amino acid derivatives that compete with glutamate for receptor binding; 2) noncompetitive antagonists, which block the cation channel; 3) glycine (a co-agonist site antagonist). Unfortunately, these compounds all interfere with normal receptor function. Administration of these drugs often produces psychotic behavior (the street drug PCP is a noncompetitive NMDA antagonist). Also, the ability to make new memory is lost, since the NMDA receptor is crucial to this process.

The present invention facilitates modulation of the redox site to prevent receptor overactivation, but this does not interfere with normal receptor function. Intermediate and long-term administration would therefore be more feasible with the present invention.

DEFINITIONS

"NMDA" means the N-methyl-D-aspartate receptor.
"GSH" means the reduced form of glutathione.
"GSSG" means oxidized glutathione.
"CNS" means the central nervous system.
"SHG" means S-hexylglutathione.
"SMG" means S-methylglutathione.
"ME" means mercaptoethanol.

SUMMARY OF THE INVENTION

The present invention relates to a method of treating various neurological and central nervous system conditions, including but not limited to pain, neurological diseases, and neuronal injury, by utilizing a compound that interacts with and modifies one of the redox sites of the NMDA receptor.

Accordingly, it is an object of the present invention to provide a method of treating central nervous system diseases and conditions in a mammal, comprising administering a compound that interacts with and modifies one of the redox sites of the NMDA receptor in said mammal.

It is another object of the present invention to provide a method of treating central nervous system diseases and conditions in a mammal, comprising administering a therapeutically effective amount of a compound that interacts with and modifies one of the redox sites of the NMDA receptor in said mammal, wherein said compound is one of the class of S-substituted glutathione derivatives.

BRIEF DESCRIPTION OF THE DRAWINGS

FIGS. 1(A and B). GSH selectively potentiates NMDA neurotoxicity. Cultures were exposed to: (A) indicated concentrations of NMDA alone or with 1 mM GSH or GSSG, or to 1 mM GSH or GSSG alone (0 $\mu$M NMDA) for 22 h (n=8–13 cultures/condition); (B) 8 $\mu$M NMDA with indicated concentrations of GSH for 22 h (n=13–14/condition). Medium LDH activity (mean±S.E.M.) in this and subsequent figures and tables is scaled to that in sister cultures continuously exposed to 300 $\mu$M NMDA (=100), which produces near-100% neuronal death without injuring glia. $P<0.01$, *$P<0.001$ vs. NMDA alone, Tukey-Kramer test (A) or Dunnett multiple comparisons test (B). FIGS. 2(A–C). Effect of S-hexylglutathione (SHG) and glutathione on potentiation of NMDA neurotoxicity by mercaptoethanol. Cultures (n=9–10/condition) were exposed to: (A) 3 $\mu$M NMDA alone, with 1 mM mercaptoethanol (ME), or with 1 mM ME plus 1 mM SHG for 25 h; (B) 6 $\mu$M NMDA alone, with 1 mM ME, or with ME plus 1 mM oxidized glutathione (GSSG) for 24 h; (C) 1.5 $\mu$M NMDA alone, with 1 mM ME, or with 1 mM ME plus 1 mM reduced glutathione (GSH) for 21 h. ***$P<0.001$ vs. NMDA alone, ###$P<0.001$ vs. NMDA plus ME, Tukey-Kramer test.

FIGS. 4(A–D). Cortical cell cultures stained with antibody to neuron specific enolase (A, B, C) or glial fibrillary acidic protein (D). (A) Twenty-four hours after exposure to azide 3 mM in glucose free buffer for 30 min; neuronal cell bodies and processes are intact and immunoreactive; (B) sister culture exposed to azide with 100 $\mu$M GSH; most neurons have degenerated; (C) culture treated with azide, 100 $\mu$M GSH, and 3 mM GSSG; most neurons have survived; (D) culture exposed to 3 mM azide with 100 $\mu$M GSH; glial monolayer surrounding areas of neuronal debris is intact. Scale bar=100 $\mu$m.

FIGS. 6(A and B). GSSG attenuates the effect of both GSH and mercaptoethanol (ME). Cultures (n=7/condition) were treated for 30 min with 3 mM azide alone or with 100 $\mu$M GSH (A) or 100 $\mu$M mercaptoethanol (B) and indicated concentrations ($\mu$M) of GSSG. Medium was sampled 24 h later. *$P<0.05$, ***$P<0.001$ vs. azide alone, ###$P<0.001$ vs. azide plus GSH or ME, Tukey-Kramer test.

FIGS. 7(A and B). SHG attenuates the effect of both GSH and mercaptoethanol. Cultures (n=7–8/condition) were exposed for 30 min to 3 mM azide alone or with 100 $\mu$M GSH or 100 $\mu$M mercaptoethanol (ME) plus indicated concentrations ($\mu$M) of SHG. ***$P<0.001$ vs. azide alone, ##$P<0.01$, ###$P<0.001$ vs. azide plus GSH or ME, Tukey-Kramer test.

FIGS. 8(A–C). Morphologic appearance of cultures after 24 h exposure to: (A) 6 $\mu$M NMDA; (B) 6 $\mu$M NMDA and 1 mM GSH; (C) 6 $\mu$M NMDA, 1 mM GSH, and 1 mM S-hexylglutathione. Cultures were stained with 0.27% trypan blue, which stains necrotic cells but is excluded by viable cells. Scale bar=100 mn.

DETAILED DESCRIPTION

In this study, the effect of extracellular glutathione on excitotoxic neuronal injury was quantitatively assessed in murine cortical cell cultures. Neuronal death due to 20–25 h exposure to 6–9/$\mu$M NMDA was markedly enhanced by 300–1000/$\mu$M reduced glutathione; kainate neurotoxicity was unaffected. Two related compounds that lack a sulfhydryl group, S-hexylglutathione and S-methylglutathione, were inactive per se but completely blocked the effect of reduced glutathione. Mercaptoethanol, a sulfhydryl reducing agent that increases NMDA receptor responses by reducing redox sites, increased NMDA neurotoxicity to a degree comparable to that of glutathione; this effect was also blocked by equimolar S-hexylglutathione and oxidized glutathione. Addition of reduced glutathione to mercaptoethanol did not further increase NMDA-induced neuronal death. These results demonstrate that reduced glutathione is an endogenous ligand at NMDA receptor redox sites. Glutathione analogs that lack a sulfhydryl group provide a novel pharmacologic approach to modulation of NMDA receptor responses.

Materials and Methods

Cortical cell culture

Murine cortical cell cultures, containing both neurons and glia, were prepared from gravid Swiss Webster mice (15–16 days gestation) as previously described. (Regan R. F. and Choi D. W. The effect of NMDA, AMPA/kainate, and calcium channel antagonists on traumatic cortical neuronal injury in culture. Brain Res 633: 236–242, 1994; Rose K., Goldberg M. P. and Choi D. W. Cytotoxicity in murine neocortical cell culture, in: Methods in Toxicology, Part A: In Vitro Biological Systems (Tyson, C. A. and Frazier J. M., ed.) 46–60. Academic Press, San Diego, 1993).

After halothane anesthesia and cervical dislocation, cortical hemispheres were removed and incubated in 0.075% (wt/vol) acetylated trypsin (Sigma T-6763) for 1 h at 37° C. Tissue was dissociated by multiple passages through a narrow bore (flamed) Pasteur pipette, and the cell suspension was plated on confluent glial cultures at a density of 2.25–2.5 hemispheres per 24 well plate. Plating medium consisted of Eagle's minimal essential medium (MEM), 5% equine serum, 5% fetal bovine serum, 2 mM glutamine, and 23 mM glucose. Cultures were incubated in 5% $CO_2$ at 37° C. Two-thirds of the culture medium was exchanged twice weekly with MEM containing 10% equine serum, 2 mM glutamine, and 23 mM glucose. Glial cell division was inhibited at 4–7 days in vitro with $10^{-5}$ M cytosine arabinoside.

Cortical glial cultures were prepared from neonatal Swiss-Webster mice. (Regan R. F. and Choi D. W.,1994). Plating density was 1 hemisphere/24 well plate.

Excitatory amino acid exposure

Experiments were conducted at 13–15 days in vitro. Cultures were exposed to excitatory amino acids in serum-free MEM containing 10 mM glucose. (Rose K., Goldberg M. P. and Choi D. W., 1993). Since thiol-containing compounds spontaneously oxidize in aqueous solutions (Held K. D. and Biaglow J. E. Mechanism for the oxygen radical-mediated toxicity of various thiol-containing compounds in cultured mammalian cells. Radiat Res 139: 15–23, 1994), glutathione and mercaptoethanol were added to cultures from stock solutions that were prepared immediately prior to use.

Assessment of injury

Cell death was estimated at the end of the exposure period by inspection under phase-contrast microscopy, and was quantified by measurement of lactate dehydrogenase (LDH) activity in the culture medium, as previously described in detail. (Regan R. F. and Panter S. S. Traumatic neuronal injury in cortical cell culture is attenuated by 21-aminosteroids. Brain Res 682: 144–150, 1995). Neuronal LDH activity was consistent in cultures prepared from the same plating, but varied somewhat from plating to plating. In order to combine the results from cultures prepared from different platings, LDH activities were scaled to those in sister cultures exposed to 300 $\mu$M NMDA (=100), which results in essentially complete neuronal death without injuring glia. The low LDH activity in the medium of sister cultures exposed to sham wash alone was subtracted from all values to obtain the LDH signal associated specifically with neurotoxin exposure. Since astrocytes are not vulnerable to excitotoxic injury in this culture system (Choi D. W., Maulucci-Gedde M. and Kriegstein A. R. Glutamate neurotoxicity in cortical cell culture. J Neurosci 7: 357–368, 1987), the contribution of astrocytic LDH to the LDH signal is negligible.

Statistical analysis

In all experiments, data were analyzed by one-way analysis of variance. Differences between groups were assessed with the Tukey-Kramer or Dunnett post hoc tests.

Materials

Reduced glutathione was purchased from Sigma Chemical Co., St Louis, Mo., U.S.A. (Catalog #G-4251, lot 74H0646, containing 0.2–0.4% GSSG; no glutamic acid detected by TLC per manufacturer's analysis). MEM and glutamine were purchased from Gibco (Life Technologies Inc., Grand Island, N.Y., U.S.A.), and serum was purchased from Hyclone, Inc., Logan, Utah, U.S.A. Culture plates were manufactured by Greiner Labortechnik and purchased from Bellco Glass, Inc., Vineland, N.J., U.S.A. All other reagents were purchased from Sigma.

Results

Figure 1:
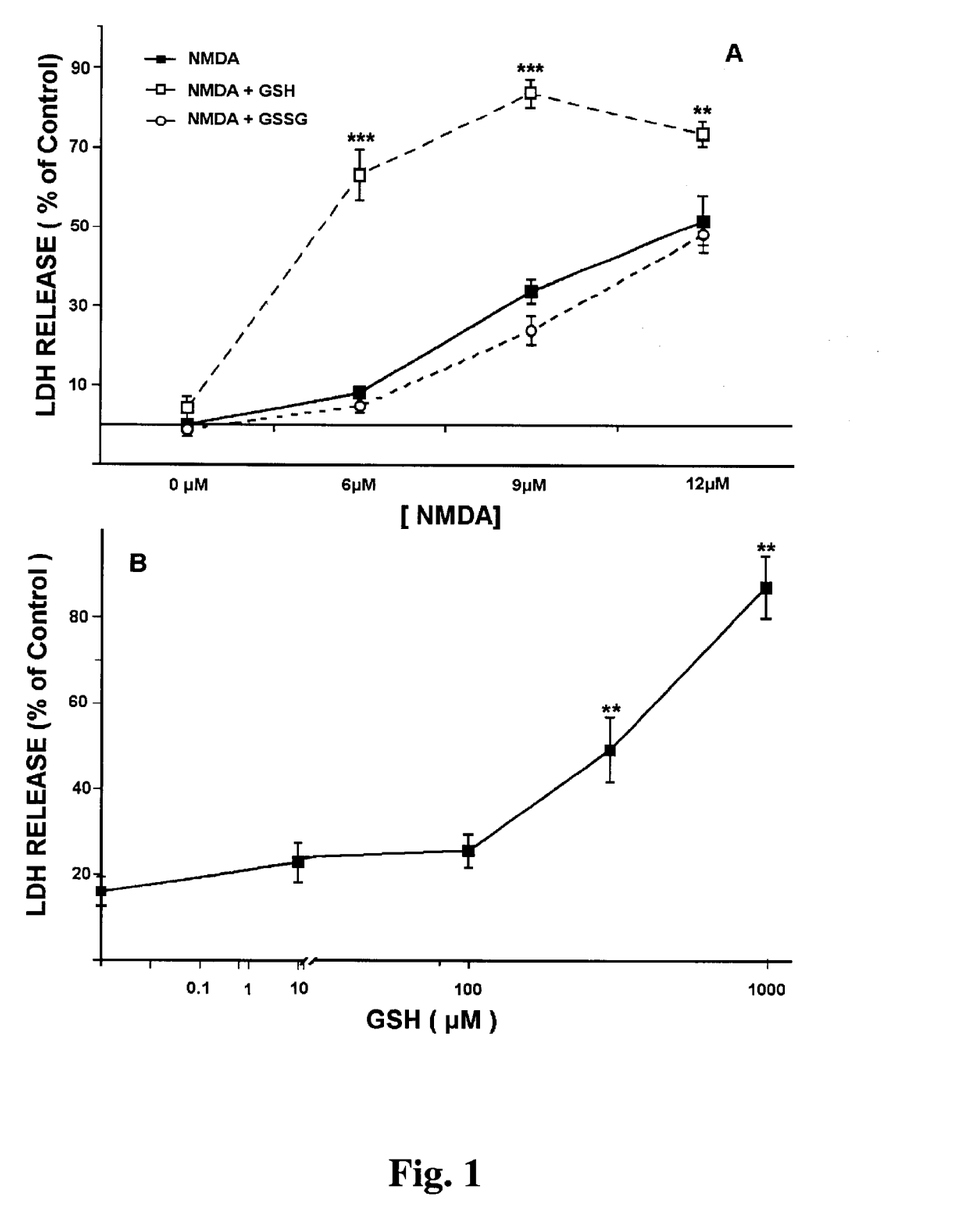

Exposure to millimolar concentrations of GSH for 20–25 h was tolerated by most neurons. In some GSH-exposed cultures, medium LDH activity tended to be higher than in sister cultures subjected to sham wash alone, suggesting very mild neuronal injury; however, this difference did not reach statistical significance (FIG. 1A, 0 $\mu$M NMDA concentration). Increasing the GSH concentration to 3–10 mM did not further increase LDH release. GSSG was nontoxic.

The neurotoxicity of low concentrations of NMDA was markedly potentiated by 0.3–1 mM GSH (FIGS. 1A,B). Although LDH release in cultures treated with 12 $\mu$M NMDA plus GSH was slightly less than in those treated with 9 $\mu$M plus GSH (FIG. 1A), this difference was not statistically significant (P>0.05, Tukey-Kramer test). Increasing the NMDA concentration to 24 $\mu$M resulted in widespread neuronal death that was not altered by GSH (Table 1). GSSG had no significant effect on NMDA toxicity, although a cytoprotective trend was observed (FIG. 1A). GSH did not alter the neurotoxicity of kainic acid, a nonselective agonist at AMPA and kainate receptors (Table 2). Cell death due to 8 $\mu$M NMDA plus GSH was completely blocked by the selective NMDA receptor antagonist MK-801 (LDH release 61.09±3.83% reduced to −1.24±1.58% by MK-801).

The disparate effects of GSH and GSSG suggested that potentiation of NMDA neurotoxicity required a sulfhydryl group. Based on data from glutathione binding studies (Lanius R. A., Shaw C. A., Wagey R. and Krieger C. Characterization, distribution, and protein kinase C-mediated regulation of [$^{35}$S]glutathione binding sites in mouse and human spinal cord. J Neurochem 63: 155–160, 1994; Ogita K. and Yoneda Y. Temperature-dependent and -independent apparent binding activities of [$^3$H]glutathione in brain synaptic membranes. Brain Res 463: 37–46, 1988), it was concluded that GSH interacts with receptors and activates or modifies these receptors via a sulfhydryl exchange reaction. To confirm this, the effects of the S-substituted glutathione derivatives S-hexylglutathione (SHG) and S-methylglutathione (SMG), which lack a sulfhydryl group and displace glutathione binding (Lanius R. A., Shaw C. A., Wagey R. and Krieger C., 1994), were investigated. SHG alone had no significant effect on NMDA neurotoxicity in this model, although, as with GSSG, a weak protective trend was observed (Table 3). However, SHG completely blocked the potentiation of neuronal death induced by GSH; equimolar GSSG had a similar effect (Table 4).

Figure 2:
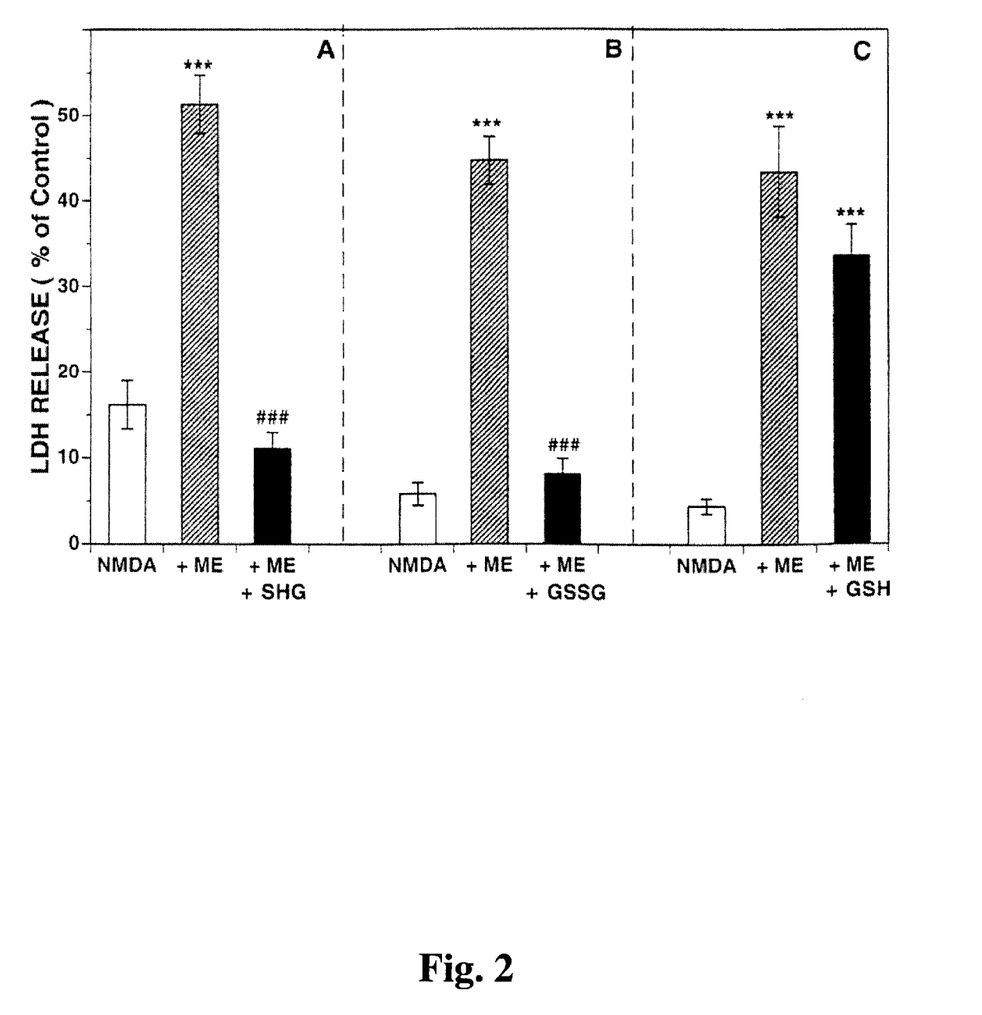

At high micromolar to millimolar concentrations, exogenous sulfhydryl reducing agents enhance NMDA receptor responses by reacting with its redox modulatory site. (Aizenman E., Lipton S. A., Loring R. H. Selective modulation of NMDA responses by reduction and oxidation. *Neuron* 2: 1257–1263, 1989). Since GSH selectively potentiated NMDA neurotoxicity, but only at high concentrations, reduction of NMDA receptor redox sites contributed to this effect. GSH analogs lacking a sulfhydryl group allosterically inhibit the action of other reducing agents. Consistent with prior observations (Majewska M. D., Bell J. A. and London E. D. Regulation of the NMDA receptor by redox phenomena: inhibitory role of ascorbate. *Brain Res* 537: 328–332, 1990), 1 mM mercaptoethanol markedly enhanced neuronal death due to exposure to low micromolar concentrations of NMDA (FIG. 2); equimolar S-hexylglutathione and GSSG completely blocked this effect, mimicking their antagonism of GSH (FIGS. 2A,B). Addition of GSH to mercaptoethanol did not further increase neuronal death (FIG. 2C); on the contrary, and in agreement with a prior observation (Janáky R., Varga V., Saransaari P. and Oja S. S. Glutathione modulates the N-methyl-D-aspartate receptor-activated calcium influx into cultured rat cerebellar granule cells. *Neurosci Lett* 156, 153–157, 1993), GSH tended to inhibit the effect of mercaptoethanol.

Spontaneous oxidation of thiol compounds in aqueous solutions produces hydrogen peroxide; in the presence of serum or transition metals, oxidative death of cultured fibroblasts results that is blocked by catalase. (Held K. D. and Biaglow J. E. Mechanism for the oxygen radical-mediated toxicity of various thiol-containing compounds in cultured mammalian cells. *Radiat Res* 139: 15–23, 1994). In order to determine whether or not this mechanism was operative in this model, catalase was added at a concentration sufficient to inhibit the neurotoxicity of the pro-oxidant hemoglobin. (Regan R. F. and Guo Y. P. Toxic effect of hemoglobin on spinal cord neurons in culture. *J Neurotrauma* 15: 645–653, 1998). No effect was observed (Table 5). GSH also potentiated injury in the presence of the potent antioxidant U74500A (Table 6), which blocks hemoglobin toxicity at low micromolar concentrations. (Regan R. F. and Panter S. S. Neurotoxicity of hemoglobin in cortical cell culture. *Neurosci Lett* 153; 219–222, 1993).

Discussion

This study provides novel evidence that high concentrations of extracellular reduced glutathione markedly enhance the vulnerability of cortical neurons in a primary culture system to NMDA. Four experimental observations support the idea of GSH as an endogenous ligand at NMDA receptor redox sites. First, GSH specifically potentiated NMDA neurotoxicity; neuronal death due to excessive AMPA/kainate receptor activation was unaffected. Second, this effect was noted only at high micromolar and millimolar GSH concentrations; similar concentrations of GSH and exogenous sulfhydryl compounds have been required for enhancement of NMDA receptor responses in other in vitro systems. (Aizenman E., Lipton S. A., Loring R. H., 1989; Janáky R., Varga V., Saransaari P. and Oja S. S., 1993; Köhr G., Eckardt S., Lüddens H., Monyer H. and Seeburg P. H. NMDA receptor channels: subunit-specific potentiation by reducing agents. *Neuron* 12: 1031–1040, 1994; Majewska M. D., Bell J. A. and London E. D. Regulation of the NMDA receptor by redox phenomena: inhibitory role of ascorbate. *Brain Res* 537: 328–332, 1990). Third, the activity of GSH appeared to be dependent on its sulfhydryl group; two GSH analogs that lack one, S-hexylglutathione (SHG) and S-methylglutathione (SMG), were inactive per se but antagonized the effect of GSH. Fourth, both SHG and GSSG also blocked the effect of mercaptoethanol, a thiol compound that increases NMDA receptor responses by interacting with redox sites (Majewska M. D., Bell J. A. and London E. D., 1990); adding GSH to mercaptoethanol did not further enhance NMDA neurotoxicity.

The results of this study are consistent with those of two prior reports. Köhr et al. (Köhr G., Eckardt S., Lüddens H., Monyer H. and Seeburg P. H., 1994) noted that millimolar concentrations of GSH potentiated glutamate-induced whole cell currents and reduced desensitization in embryonic kidney cells expressing recombinant NR1-NR2A receptors, but not in cells expressing NR1-NR2B, -NR2C, or -NR2D receptors. In cultured cerebellar granule cells, Janáky et al. (Janáky R., Varga V., Saransaari P. and Oja S. S., 1993) observed that GSH did not alter basal $^{45}Ca^{2+}$ influx, but increased that induced by glutamate or NMDA exposure. However, in studies by Gilbert et al. and Sucher and Lipton, GSH had no effect on native NMDA receptor responses in cultured forebrain, cortical, or retinal neurons, although GSSG was inhibitory. (Gilbert K. R., Aizenman E. and Reynolds I. J. Oxidized glutathione modulates N-methyl-D-aspartate- and depolarization-induced increases in intracellular $Ca^{2+}$ in cultured rat forebrain neurons. *Neurosci Lett* 133; 11–14, 1991; Sucher N. J. and Lipton S. A. Redox modulatory site of the NMDA receptor-channel complex: regulation by oxidized glutathione. *J Neurosci Res* 30: 582–591, 1991). The latter group also observed that both GSH and GSSG attenuated NMDA neurotoxicity. (Levy D. I., Sucher N. J. and Lipton S. A. Glutathione prevents N-methyl-D-aspartate receptor-mediated neurotoxicity. *Neuroreport* 2; 345–347, 1991). These discordant results may reflect variability in receptor subunit expression in different in vitro systems. If the NR2A subunit is not expressed, GSH may not interact with redox sites, but beneficial antioxidant or other actions may persist. It is also noteworthy that modulation of receptor responses by reducing agents develops rather slowly, and may require up to twenty minutes for complete manifestation. (Köhr G., Eckardt S., Lüddens H., Monyer H. and Seeburg P. H., 1994). In the negative electophysiologic studies mentioned above, cultures were pretreated with GSH for 100–200 seconds prior to NMDA exposure.

During CNS ischemia and other disease states associated with depolarization, release of glutathione is rapidly and substantially increased (Landolt H., Lutz T. W., Langemann H., Stäuble D., Mendelowitsch A., Gratzl O. and Honegger C. G. Extracellular antioxidants and amino acids in the cortex of the rat: monitoring by microdialysis of early ischemic changes. *J Cereb Blood Flow Metab* 12: 96–102, 1992; Zängerle L., Cuénod M., Winterhalter K. H. and Do K. Q. Screening of thiol compounds: depolarization-induced release of glutathione and cysteine from rat brain slices. *J Neurochem* 59: 181–189, 1992); extracellular levels are likely further augmented by leakage through disrupted cell membranes. Enhancement of NMDA receptor responses may then increase neuronal loss. The present data show that this process can be antagonized by an S-substituted, redox neutral derivative of glutathione. This and related compounds provide an alternate and potentially less toxic pharmacologic approach that limit acute excitotoxic injury.

Materials and Methods for Inducing Chemical Hypoxia and Glucose Deprivation

Primary cultures containing both cortical neurons and glia were prepared from gravid Swiss Webster mice as previously described. (Regan, R. F. and Choi, D. W., The effect of NMDA, AMPA/kainate, and calcium channel antagonists on traumatic cortical neuronal injury in culture, Brain Res, 633: 236–242, 1994). Plating medium consisted of Eagle's minimal essential medium (MEM), 5% equine serum, 5% fetal bovine serum, 2 mM glutamine, and 23 mM glucose. Cultures were incubated in 5% $CO_2$ at 37° C. Two-thirds of the culture medium was exchanged twice weekly with MEM containing 10% equine serum, 2 mM glutamine, and 23 mM glucose. Glial cell division was inhibited at 4–7 days in vitro with $10^{-5}$ M cytosine arabinoside.

Chemical hypoxia was induced with 3 mM azide, which unlike cyanide is not volatile and has little effect on copper-zinc and manganese superoxide dismutases at low millimolar concentrations. (Misra, H. P. and Fridovich, I., Inhibition of superoxide dismutases by azide, Arch Biochem Biophys 189: 317–322, 1978). Experiments were conducted at 13–16 days in vitro in a glucose-free buffer containing 116 mM NaCl, 5.4 mM KCl, 1.8 mM $CaCl_2$, 1 mM $NaH_2PO_4$, 26.2 mM $NaHCO_3$, 0.8 mM $MgSO_4$, and amino acids (MEM amino acids, Sigma Chemical Co., St. Louis, Mo., U.S.A.). After incubation for 30–90 min at 37° C. in 5% $CO_2$, cultures were washed into MEM containing 10 mM glucose and were returned to the incubator. Since GSH spontaneously oxidizes in aqueous solutions (Held, K. D. and Biaglow, J. E., Mechanism for the oxygen radical-mediated toxicity of various thiol-containing compounds in cultured mammalian cells, Radiat Res, 139: 15–23, 1994), it was added to cultures from stock solutions that were prepared immediately prior to use. GSH was purchased from Sigma (Catalog #G-4251, lots 74H0646 and 87H0400, containing<1% GSSG; no glutamic acid detected by TLC per manufacturer's analysis).

Cell death was estimated 21–25 h after azide exposure by inspection under phase-contrast microscopy, and was quantified by assaying lactate dehydrogenase (LDH) activity in the medium, as previously described. (Regan, R. F. and Panter, S. S., Traumatic neuronal injury in cortical cell culture is attenuated by 21-aminosteroids, Brain Res, 682: 144–150, 1995). Medium LDH in this culture system is an accurate marker of neuronal death that correlates well with cell counts. (Koh, J. Y. and Choi, D. W., Vulnerability of cultured cortical neurons to damage by excitotoxins: Differential susceptibility of neurons containing NADPH-diaphorase, J Neurosci 8: 2153–2163, 1988). LDH activity was consistent in cultures prepared from the same plating, but varied somewhat from plating to plating. In order to combine the results from cultures prepared from different platings, LDH activities in all experiments were scaled to those in sister cultures exposed for 21–25 h to 300 μM NMDA (=100), which results in essentially complete neuronal death without injuring glia. (Koh, J. Y. and Choi, D. W., 1988). The LDH activity in the medium of sister cultures exposed to sham wash alone was subtracted from all values to obtain the LDH signal associated specifically with neurotoxin exposure. Since brief azide exposure does not produce glial death, the contribution of glial LDH to the LDH signal is negligible.

Data were analyzed by one-way analysis of variance. Differences between groups and a single mean were assessed with the Dunnett multiple comparisons test; when groups were compared to more than one mean, the Tukey-Kramer post hoc test was used.

Results

Figure 3:
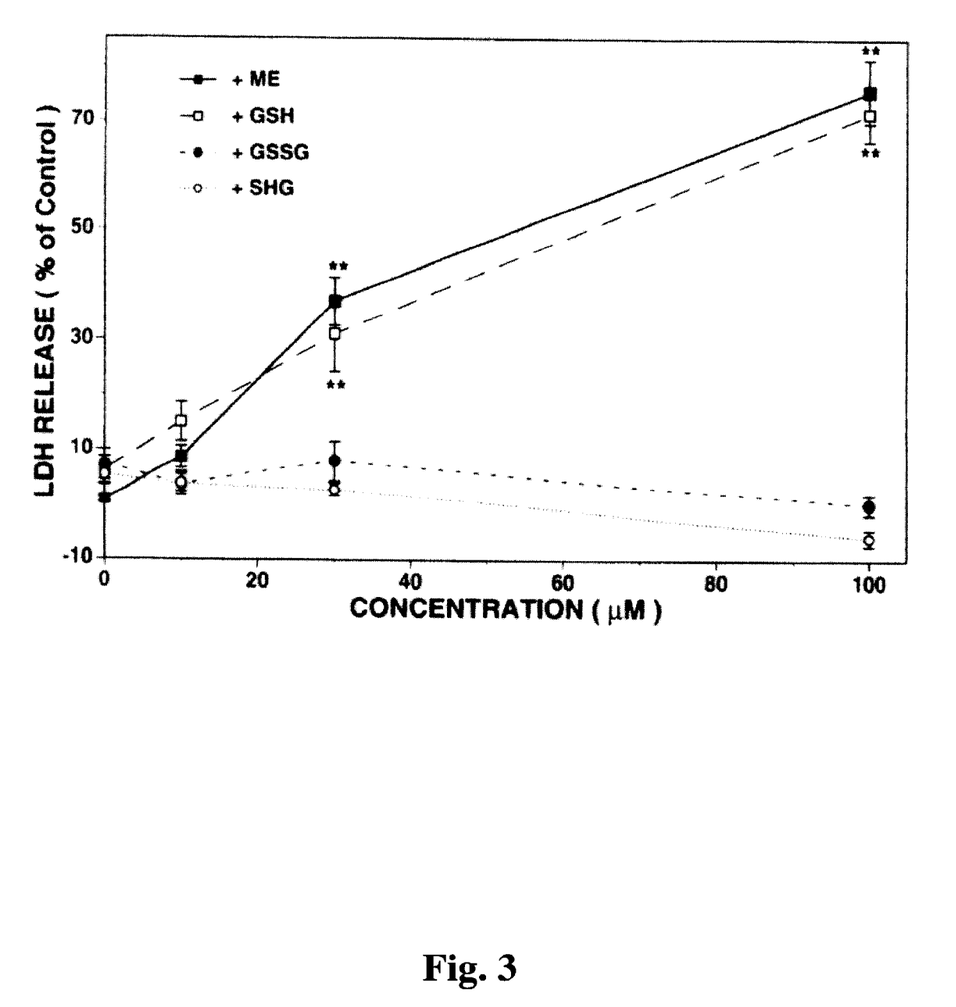
FIG. 3. GSH and mercaptoethanol (ME) potentiate azide neurotoxicity in glucose-free buffer; GSSG and SHG are ineffective. Cultures (n=8/condition) were exposed to azide 3 mM with indicated concentrations of ME, GSH, GSSG, or SHG for 30 min, then washed into MEM with 10 mM glucose. Medium was sampled for LDH assay 24–25 h later. Medium LDH (mean±S.E.M.) in this and subsequent figures and tables is scaled to that in sister cultures continuously exposed to 300 $\mu$M NMDA (=100), which produces near-complete neuronal death without injuring glia. **$P<0.01$ vs. azide alone, Dunnett multiple comparisons test.
Figure 4:
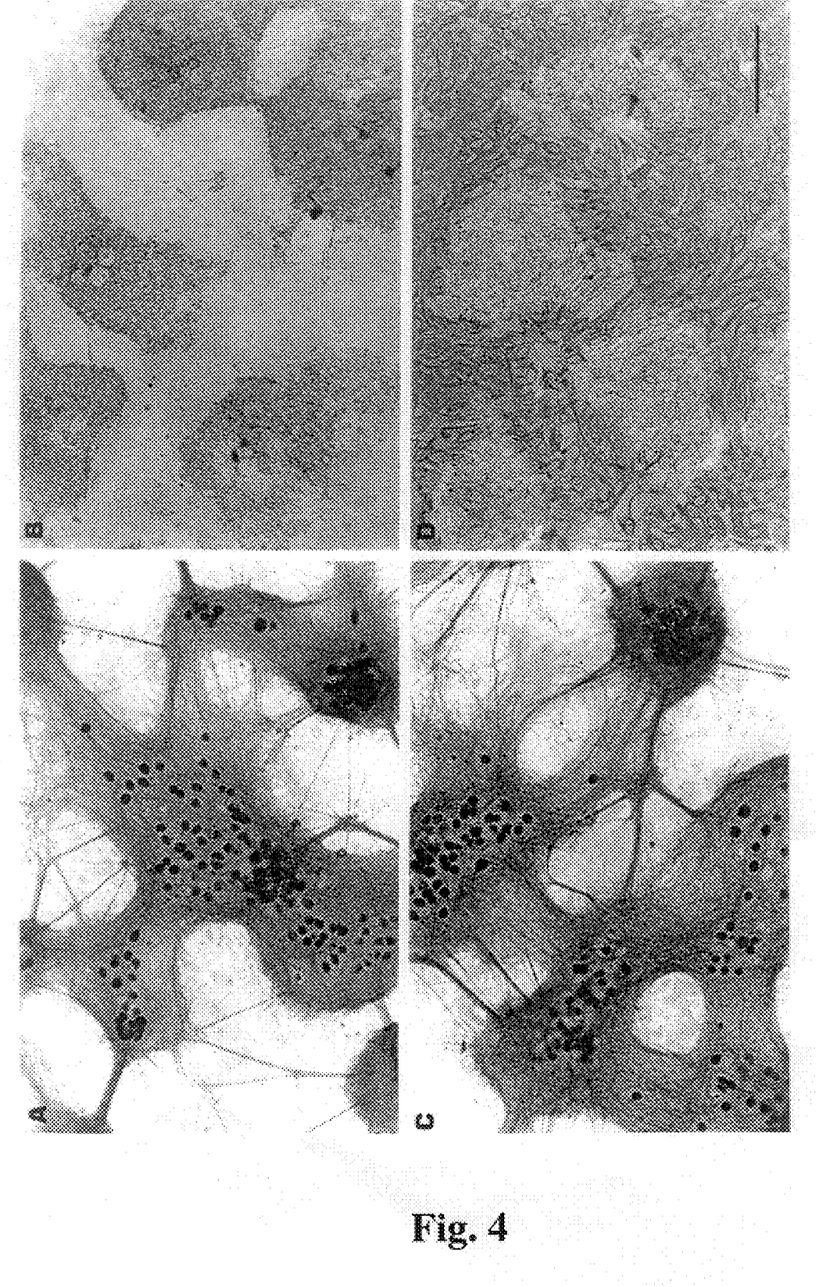

Exposure to 3 mM azide in glucose-free medium for 30 minutes was tolerated by most neurons, with little neuronal LDH release over the subsequent day (FIG. 3, GSH concentration=0; FIG. 4A). When GSH was present during azide exposure, neuronal injury increased in a concentration dependent fashion (FIGS. 3 and 4B), with death of 71.6±5.1% at 100 μM; glia were not injured (FIG. 4D). Treatment with 100 μM GSH alone in MEM for 30 minutes was nontoxic (LDH values in sister cultures: 127.6±11.0 units/ml in sham washed controls, 121.0±16.0 units/ml in cultures exposed to 100 μM GSH for 30 min, and 722.5±32.2 units/ml in cultures subjected to full neuronal kill). The sulfhydryl compound mercaptoethanol had a concentration-toxicity profile that was similar to GSH (FIG. 3), as did dithiothreitol; 30 min exposure to 10–100 μM of either agent in MEM without azide was likewise nontoxic. Cell death was not increased by either GSSG or S-hexylglutathione (SHG), a GSH analogue that lacks a sulfhydryl group.

Figure 5:
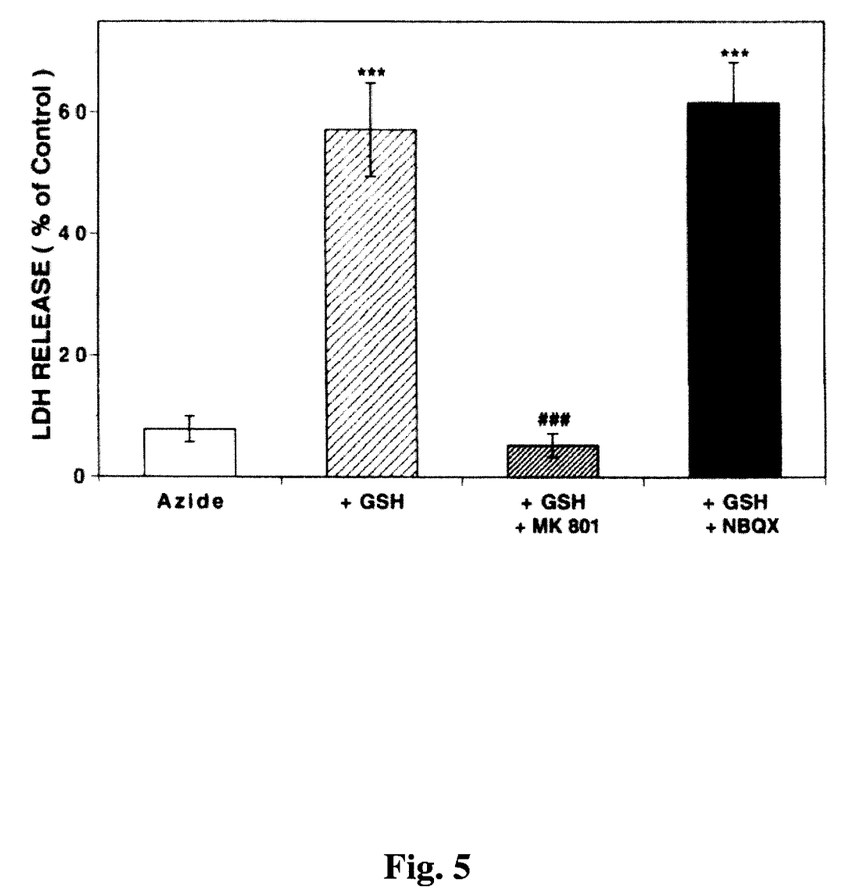
FIG. 5. Potentiation of azide toxicity/glucose deprivation by GSH is blocked by MK-801 but not by NBQX. Cultures (n=12/condition) were treated with azide alone, with GSH 100 $\mu$M, or with GSH plus 10 $\mu$M MK-801 or 10 $\mu$M NBQX for 30 min. After washout into MEM with 10 mM glucose, medium was sampled 21 h later. ***$P<0.001$ vs. azide alone, ###$P<0.001$ vs. azide plus GSH, Tukey-Kramer multiple comparisons test.

In this culture system, high micromolar concentrations of exogenous GSH selectively potentiate N-methyl-D-aspartate (NMDA) neurotoxicity. (Regan, R. F. and Guo, Y. P., Extracellular glutathione potentiates excitotoxic neuronal injury in cortical cell culture, Soc Neurosci Abstr, 24: 462, 1998).In order to determine if its effect on azide toxicity/glucose deprivation was via an excitotoxic mechanism, cultures were treated with the selective NMDA receptor antagonist MK-801 or the AMPA/kainate antagonist NBQX (1,2,3,4-tetrahydro-6-nitro-2,3-dioxo-benzo[f]quinoxaline-7-sulfonamide). Neuronal death was blocked by a saturating concentration (10 μM) of MK-801; NBQX had no effect (FIG. 5).

Figure 6:
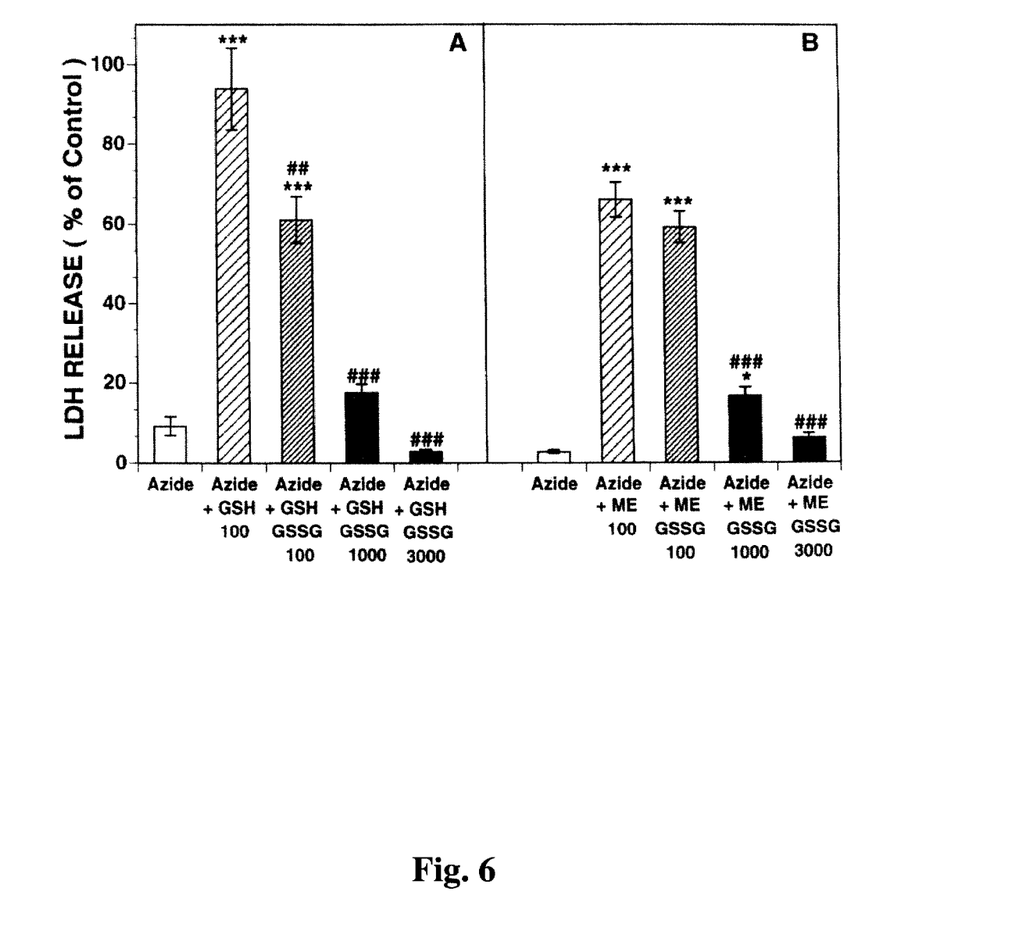
Figure 7:
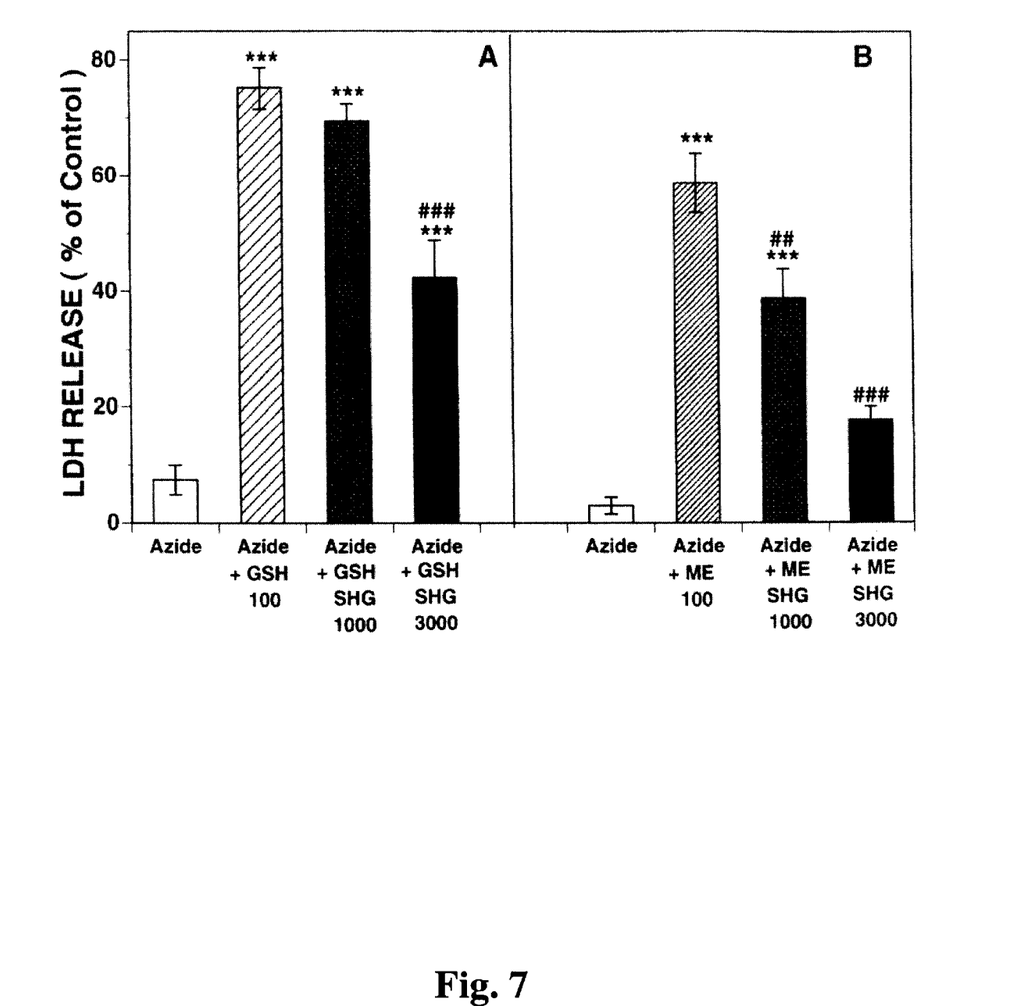

In a prior study, we observed that potentiation of NMDA neurotoxicity by sulfhydryl reducing agents was antagonized by GSSG or SHG, although these agents did not attenuate NMDA neurotoxicity per se. (Regan, R. F. and Guo, Y. P., 1998). Both compounds were also effective in the present model. Equimolar GSSG (100 μM) provided weak and somewhat variable neuroprotection; at 1–3 mM, a robust effect was observed (FIG. 4C, FIG. 6). SHG was also neuroprotective but less potent, decreasing neuronal death moderately at 1–3 mM (FIG. 7). GSSG had no significant effect on neuronal death induced by increasing azide exposure to 60–90 min in the absence of GSH, although considerable variability was noted (Table 7).

Potentiation of NMDA receptor responses by GSH and other sulfhydryl compounds has been hypothesized to be due to zinc chelation. (Paoletti, P., Ascher, P. and Neyton, J., High-affinity zinc inhibition of NMDA NR1-NR2A receptors, J Neurosci 17: 5711–5725, 1997). If this mechanism is valid in this model, then other zinc chelators should have a similar effect. Ethylenediaminetetraacetic acid (EDTA) is a hydrophilic compound that avidly chelates extracellular zinc in calcium containing solutions. (Klaasen, C. D., Heavy metals and heavy metal antagonists. In: Hardman J G, Limbird L E (Ed.), Goodman and Gilman's The Pharmacological Basis of Therapeutics, McGraw-Hill, New York, p. 1664, 1996). When cultures were exposed to azide with EDTA rather than GSH, neuronal death was not increased (Table 8). EDTA had no effect when added to cultures with both azide and GSH.

Discussion

This study shows that normally nontoxic concentrations of extracellular GSH markedly increase the vulnerability of cortical neurons to combined chemical hypoxia and glucose deprivation. Since neuronal death was prevented by a selective NMDA receptor antagonist, these results are in general agreement with our prior observation that exogenous GSH potentiates the toxicity of NMDA. (Regan, R. F. and Guo, Y. P., 1998). However, the effective GSH concentrations in the latter study (300–1000 µM) were an order of magnitude higher than those observed here. If GSH increases the probability of neuronal depolarization, then this discrepancy may reflect the inability of energy-depleted neurons to compensate due to cation pump inactivation.

It is important to note that low millimolar GSH concentrations are present in both glia and neurons. (Rice, M. E. and Russomenna, I., Differential compartmentalization of brain ascorbate and glutathione between neurons and glia, *Neuroscience* 82: 1213–1223, 1998). Basal release by cortical neurons is quantitatively comparable to that of glutamate and increases threefold with depolarization. (Zängerle, L., Cuénod, M., Winterhalter, K. H. and Do, K. Q., Screening of thiol compounds: depolarization-induced release of glutathione and cysteine from rat brain slices, *J Neurochem*, 59: 181–189, 1992). The massive depolarization that accompanies ischemia (Siesjö, B. K., Katsura, K, Zhao, Q., Folbergrova, J., Pahlmark, K., Siesjö, P., and Smith, M., Mechanisms of secondary brain damage in global and focal ischemia: a speculative synthesis, *J Neurotrauma* 12: 943–956, 1995) should therefore rapidly elevate extracellular levels. Consistent with this view, Landolt et al. observed that microdialysate GSH peaked within 30 minutes of middle cerebral artery occlusion and remained elevated throughout the 3 hour observation period. (Köhr, G., Eckardt, S., Lüddens, H., Monyer, H. and Seeburg, P. H., NMDA receptor channels: subunit-specific potentiation by reducing agents, *Neuron*, 12: 1031–1040, 1994). During this interval, both Rehncrona et al. (Rehncrona, S., Folbergrova, J., Smith, D. S. and Siesjö, B. K., Influence of complete and pronounced incomplete cerebral ischemia and subsequent recirculation on cortical concentrations of oxidized and reduced glutathione in the rat, *J Neurochem* 34: 477–486, 1980) and Slivka and Cohen (Slivka, A. and Cohen, G., Brain ischemia markedly elevates levels of the neurotoxic amino acid, cysteine, *Brain Res*, 608: 33–37, 1993) noted a significant decline in tissue GSH levels without a corresponding rise in GSSG, suggesting that GSH was not merely being consumed by reacting with cellular peroxides. Depolarization-induced GSH release would likely be later augmented by leakage through the disrupted membranes of necrotic cells, due to its high transmembrane concentration gradient.

Regardless of the precise molecular mechanisms involved, the present data suggest that extracellular GSH is a previously unrecognized mediator of acute neuronal injury. Pharmacologic strategies that antagonize its effect decrease excitotoxic cell death without the deleterious consequences of NMDA receptor blockade.

Figure 8:
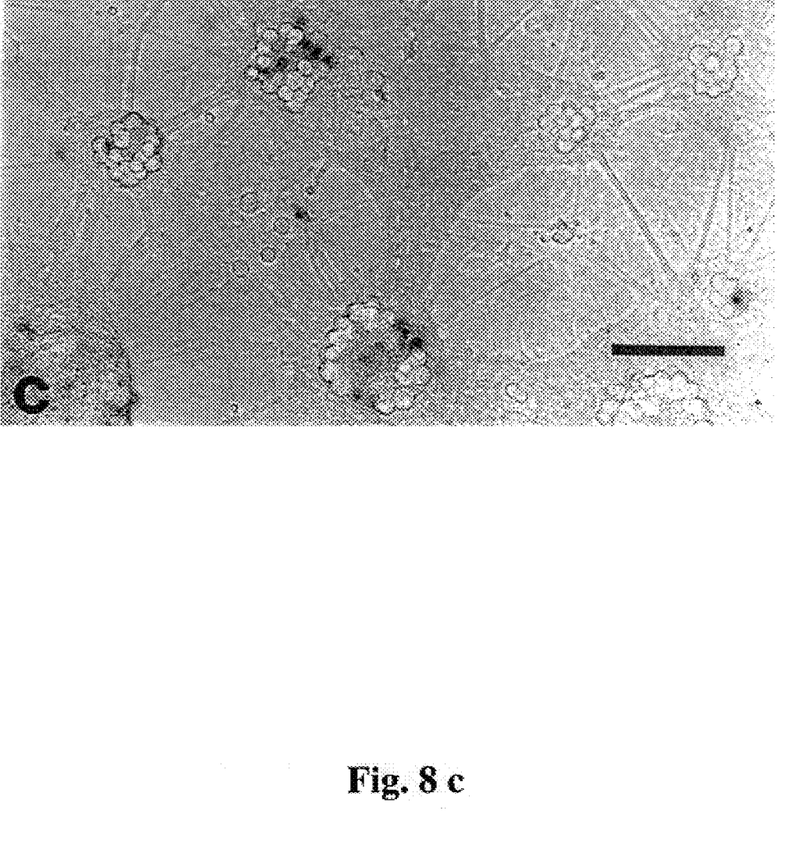
Figure 8A:
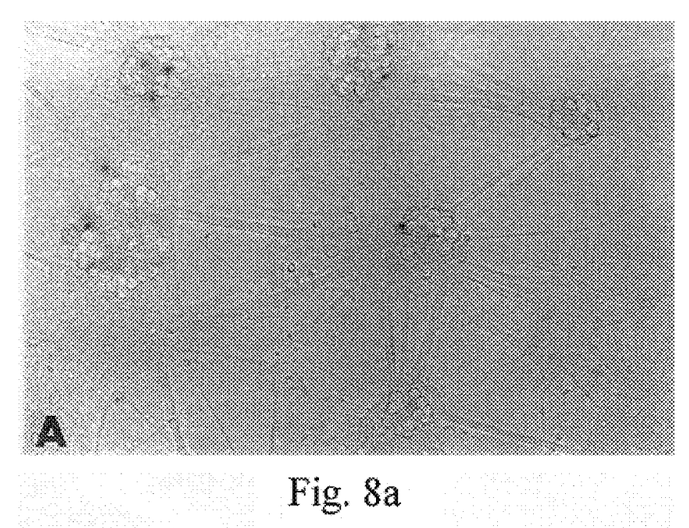
Figure 8B:
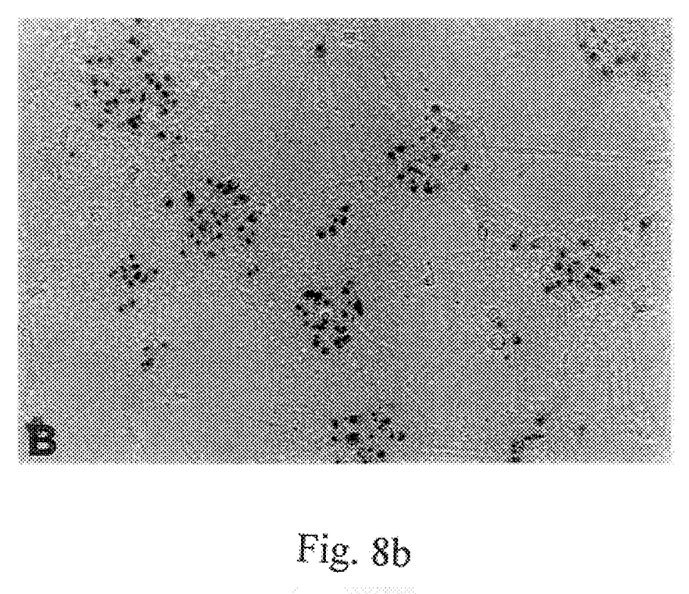
Figure 9:
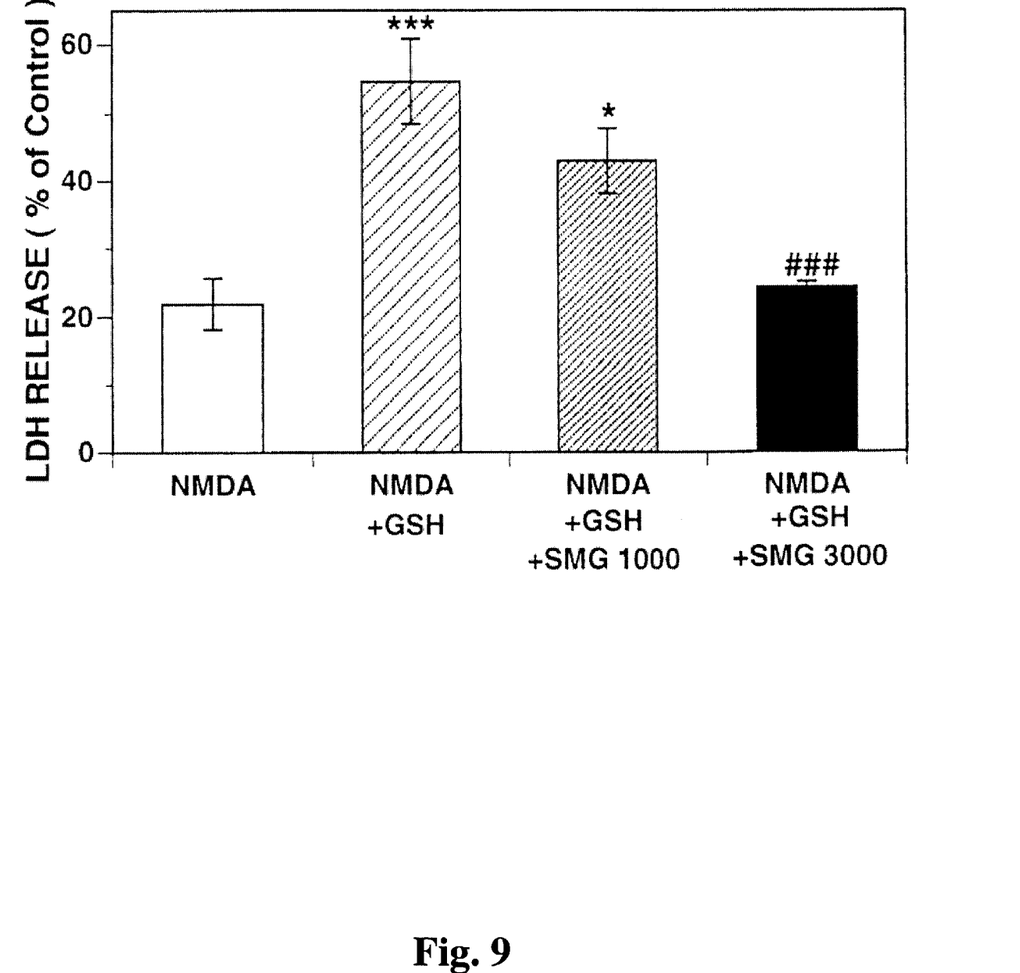
FIG. 9. S-methylglutathione (SMG) blocks the potentiation of excitotoxic injury by glutathione. Cultures (n=4/condition) were exposed for 20 h to 7 $\mu$M NMDA alone, with reduced glutathione (GSH) 300 $\mu$M, or with NMDA alone, GSH, and indicated concentrations ($\mu$M) of SMG. *$P<0.05$, ***$P<0.001$ vs. cultures exposed to NMDA alone, ###$P<0.001$ vs. cultures exposed to NMDA plus GSH. Tukey-Kramer test.

FIGS. 8 and 9 show additional details of results of experiments. FIG. 8 is another view of the morphologic appearance of cell cultures. FIG. 9 shows experimental results with SMG.

TABLE 1

Reduced glutathione in severe excitotoxic injury

| Condition | LDH release (% of control) |
|---|---|
| NMDA 24 µM | 86.22 ± 4.46 |
| NMDA 24 µM + GSH 1 mM | 93.27 ± 3.97 | n = 10 cultures/condition.

TABLE 2

Reduced glutathione does not potentiate kainate neurotoxicity

| Condition | LDH release (% of Control) |
|---|---|
| Kainate 10 µM | 18.04 ± 1.67 |
| Kainate 10 µM + GSH 1 mM | 21.93 ± 3.31 |
| Kainate 30 µM | 52.67 ± 1.74 |
| Kainate 30 µM + GSH 1 mM | 59.82 ± 2.41 |

Cultures were exposed to kainate alone or with 1 mM GSH for 25–26 h (n = 12/condition).

TABLE 3

S-Hexylglutathione blocks the effect of reduced glutathione

| Condition | LDH release (% of control) |
|---|---|
| NMDA 8 µM | 31.24 ± 5.56 |
| NMDA 8 µM + GSH 1 mM | 95.28 ± 6.24* |
| NMDA 8 µM + GSH 1 mM + SHG 1 mM | 36.01 ± 3.76† |
| NMDA 8 µM + SHG 1 mM | 18.04 ± 4.35† |

Medium LDH (mean ± S.E.M.) in cultures exposed to the indicated concentrations of NMDA, GSH and SHG for 20–21 h (n = 8/condition).
*$P < 0.001$ vs NMDA alone. †$P < 0.001$ vs NMDA + GSH. Tukey-Kramer test.

TABLE 4

Oxidized glutathione blocks the effect of reduced glutathione

| Condition | LDH release (% of control) |
|---|---|
| NMDA 8 µM | 21.98 ± 3.49 |
| NMDA 8 µM + GSH 1 mM | 73.61 ± 5.09* |
| NMDA 8 µM + GSH 1 mM + GSSG 10 µM | 76.51 ± 5.93* |
| NMDA 8 µM + GSH 1 mM + GSSG 100 µM | 52.74 ± 4.32*† |
| NMDA 8 µM + GSH 1 mM + GSSG 1000 µM | 17.55 ± 1.85‡ |

Cultures (n = 11–12/condition) were exposed to the indicated compounds for 21 h.
*$P < 0.001$ vs NMDA alone; †$P < 0.01$, ‡$P < 0.001$ vs NMDA + GSH. Tukey-Kramer test.

TABLE 5

Catalase does not attenuate the potentiation of N-methyl-D-aspartate neurotoxicity by reduced glutathione

| Condition | LDH release (% of control) |
|---|---|
| NMDA 7 µM | 18.03 ± 3.12 |
| NMDA 7 µM + GSH 1 mM | 87.40 ± 6.31* |
| NMDA 7 µM + GSH 1 mM + catalase 10 U/ml | 94.08 ± 2.98* |
| NMDA 7 µM + GSH 1 mM + catalase 100 U/ml | 82.92 ± 4.72* |

Medium LDH (mean ± S.E.M.) after 22 h exposure to the indicated compounds (n = 9 cultures/condition).
*$P < 0.001$ vs NMDA alone, Tukey-Kramer test.

TABLE 6

Reduced glutathione potentiates N-methyl-D-aspartate neurotoxicity in the presence of the antioxidant U74500A

| Condition | LDH release (% of control) |
|---|---|
| NMDA 7 µM | 18.42 ± 0.99 |
| NMDA 7 µM + U74500A 10 µM | 12.99 ± 1.30 |

TABLE 6-continued

Reduced glutathione potentiates N-methyl-D-aspartate neurotoxicity in the presence of the antioxidant U74500A

| Condition | LDH release (% of control) |
|---|---|
| NMDA 7 $\mu$M + U74500A 10 $\mu$M + GSH 300 $\mu$M | 33.69 ± 2.96*† |

Exposure duration = 24 h, n = 10 cultures/condition.
*$P < 0.001$ vs NMDA alone, †$P < 0.001$ vs NMDA + U74500A, Tukey-Kramer test.

I claim:

1. A method of treating central nervous system diseases and conditions in a mammal, comprising administering a therapeutically effective amount of a compound that interacts with and modifies one of the redox sites of the NMDA receptor in said mammal, wherein said compound is one of the class of S-substituted glutathione derivatives.

* * * * *